United States Patent [19]

Bock et al.

[11] Patent Number: 4,487,963
[45] Date of Patent: Dec. 11, 1984

[54] ENANTIOSELECTIVE SYNTHESIS OF 4-AMINO-3-HYDROXY-2,4-(DISUBSTITUTED)PENTANOIC ACID

[75] Inventors: Mark G. Bock, Hatfield; Robert M. DiPardo, Lansdale, both of Pa.

[73] Assignee: Merck & Co., Inc., Rahway, N.J.

[21] Appl. No.: 455,100

[22] Filed: Jan. 3, 1983

[51] Int. Cl.$^3$ ............................................ C07C 101/30
[52] U.S. Cl. .................................. 562/567; 560/160; 560/170; 548/215
[58] Field of Search ........................ 562/567; 560/160

[56] References Cited

PUBLICATIONS

McOmie, "Protective Groups in Organic Chemistry," pp. 43, 72, 73 and 83–93 (1973).
Roberts, "Basic Principles of Organic Chemistry," pp. 287–291 and 301–304 (1964).
Evans et al., J. Am. Chem. Soc., (1981) 103, 2127.
J. Am. Chem. Soc., (1982) 104, 1737.
Takita et al., Tetrahedron Letters (1982) 23, 521.
Narita et al., Tetrahedron Letters (1982) 23,525.
J. Org. Chem., (1981) 46, 1232.
J. Amer. Chem. Soc., (1980) 102, 1452.
J. Antibiotics (1974) 27,356.

Primary Examiner—Michael L. Shippen
Attorney, Agent, or Firm—Daniel T. Szura; Raymond M. Speer

[57] ABSTRACT

4-Amino-3-hydroxy-2,4-(disubstituted)pentanoic acids of the formula:

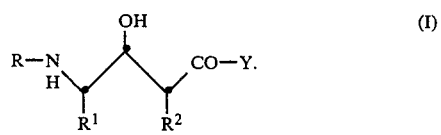

(I)

useful as intermediates in preparing antibacterial compounds, are synthesized enantiospecifically by acylation of a chiral enolate with an optically active acylating agent. The resulting product is reduced stereospecifically to afford a protected form of the desired product, which contains three adjacent asymmetric centers of known configuration. The synthesis may be illustrated as follows:

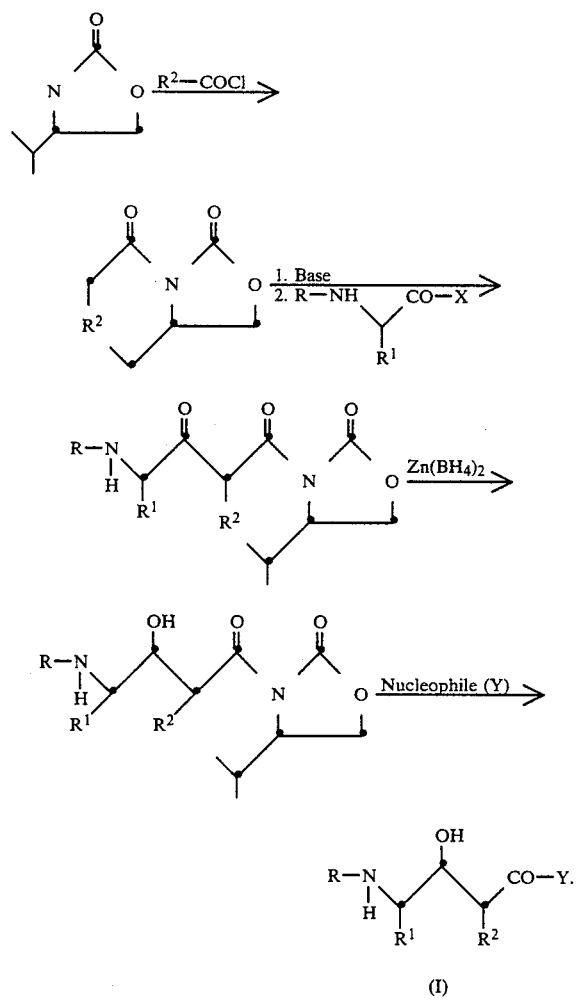

(I)

1 Claim, No Drawings

ENANTIOSELECTIVE SYNTHESIS OF 4-AMINO-3-HYDROXY-2,4-(DISUBSTITUTED)-PENTANOIC ACID

BACKGROUND OF THE INVENTION

1. Field of the Invention

The present invention is concerned with a novel method of preparation for 4-amino-3-hydroxy-2,4-(disubstituted)pentanoic acids having the following configuration: (2S, 3S, 4R).

The pentanoic acids prepared by the novel method of the present invention are useful as intermediates in preparing antibacterial compounds. Particularly, (2S, 3S, 4R)-4-amino-3-hydroxy-2-methylpentanoic acid (AHMPA) is a key element in the synthesis of the antitumor, antibiotic bleomycin $A_2$, thus making its availability in high enantiomeric purity desirable.

2. Brief Description of the Prior Art

Evans et al., *J. Am. Chem. Soc.*, (1981 103, 2127, and *J. Am. Chem. Soc.*, (1982) 104, 1737, describes enantioselective synthesis of α-substituted carboxylic acid derivatives utilizing the asymmetric alkylation reactions of chiral imide enolates derived from N-acyl oxazolidones. However, enantioselective acylation is not described, nor are the remaining novel steps of the method of the present invention suggested.

Takita et al., *Tetrahedron Lett.*, (1982) 23, 521, describes the total synthesis of bleomycin $A_2$, but nowhere suggests the method of the present invention.

Narita et al., *Tetrahedron Lett.*, (1982) 23, 525, describes stereoselective synthesis of (2S, 3S, 4R)-4-amino-3-hydroxy-2-methylpentanoic acid (AHMPA) through aldol condensation of (R)-2-aminopropionaldehyde derivatives and E-vinyloxyboranes; Ohgi and Hecht, *J. Org. Chem.*, (1981) 46, 1232, describes preparation of AHMPA from L-rhamnose as an alternative to the stereoselective aldol condensation; Levin et al., *J. Amer. Chem. Soc.*, (1980) 102 1452, describes obtaining the desired 2S, 3S, 4R configuration by cyclization to the lactam, epimerization, hydrolysis, and fractional crystallization; and Yoshioka et al., *J. Antibiotics*, (1974) 27, 356 describes a biosynthetic-like synthesis of (2S, 3S, 4R)-4-amino-3-hydroxy-2-methyl-n-valeric acid. However, none of the above references suggests the method of the present invention.

DETAILED DESCRIPTION OF THE INVENTION AND PREFERRED EMBODIMENTS

In accordance with the present invention there is provided a method of preparing a compound of the formula:

$$\text{R—N(H)—CH(R}^1\text{)—CH(OH)—CH(R}^2\text{)—CO—Y} \quad \text{(I)}$$

wherein:

R is hydrogen or an acyl, amino-protecting group;

$R^1$ and $R^2$ are each independently selected from the group consisting of hydrogen; loweralkyl; arloweralkyl; and arloweralkyl wherein the aryl group is substituted with one or two members selected from the group consisting of halo, loweralkoxy, and diloweralkylamino; and Y is a nucleophilic group;

and the configuration of the compound is (2S, 3S, 4R); comprising the following steps:

(a) treating an N-acyloxazolidinone of the formula:

$$\text{(II.)}$$

with a very strong base, followed by reaction with a compound of the formula:

$$\text{R—N(H)—CH(R}^1\text{)—CO—X} \quad \text{(III.)}$$

wherein X is a leaving group, and the compound has a D-configuration;

(b) reducing the product of Step (a) with zinc borohydride or hydrogen to form the compound of the formula:

$$\text{(IV)}$$

having a (2S, 3S, 4R) configuration; and (c) treating the product of Step (b) with a nucleophilic reagent to give a compound of Formula I having a (2S, 3S, 4R) configuration.

The loweralkyl substituents recited above represent any of the variables of straight or branched hydrocarbon radicals of from one to six carbon atoms, such as methyl, ethyl, i-propyl, t-butyl, and the like.

The loweralkoxy substituent represents a loweralkyl group as described above attached through an oxygen bridge.

The aryl substituent represents phenyl or naphthyl.

Halo means chloro, bromo, or fluoro.

The leaving group represents any radical suitable for carrying out the acylation of Step A of the method of the present invention described herein. For example, where the reactant of Formula III is an acid halide, the leaving group will be chloro or bromo. While the anhydride leaving group is preferred, other groups such as pentafluorophenoxy or dinitrophenoxy may be used.

The acyl, amino-protecting group includes any of the acyl radicals commonly employed or which might be employed, in protecting the amino portion of an amino acid during preparation of peptides, or during other reactions. For example, the acyl, amino-protecting group may be t-butyloxycarbonyl, benzyloxycarbonyl, and the like.

The nucleophilic group represents any radical from a nucleophilic reagent which will afford cleavage of the oxazolidinone auxilliary as recited in Step (C) above for the method of the present invention. For example, the nucleophilic reagent, potassium hydroxide, may be employed and gives the nucleophilic group $^{\ominus}OH$ and the compound of Formula I in acid form. The nucleophilic reagent, sodium methoxide, gives the nucleophilic group $^{\ominus}OCH_3$ and the compound of Formula I as the methyl ester. Hydrazine may also be employed as the nucleophilic reagent and provides the compound of Formula I as the hydrazide, useful in further coupling reactions.

Typical compounds of Formula I which may be prepared by the enantioselective method of the present invention are the following:

methyl (2S,3S,4R)-4-t-butyloxycarbonylamino-3-hydroxy-2-methylpentanoate;

(2S,3S,4R)-4-t-butyloxycarbonylamino-3-hydroxy-6-methylheptanoic acid;

In Step A of the method of the present invention, the starting material is an N-acyloxazolidinone which may be prepared in accordance with known methods whereby the desired $R^2$ substituent is obtained. For example, 3-S-i-propyl-1,4-oxazolidin-5-one is reacted with i-propionyl chloride to provide a desired starting material. The 3-S-i-propyl group of the oxazolidinone is a chiral auxilliary which determines the chirality of the $R^2$ (2-position) substituent. Thus, the 3-S-i-propyl-1,4-oxazolidin-5-one, prepared from D-valine, will provide a 2-S compound of Formula I.

In Step A the desired oxazolidinone starting material is treated with a very strong base. A very strong base which is preferred is lithium diisopropylamide. Another suitable very strong base is lithium hexamethyldisilazide. The reaction is carried out at a temperature of from −55° to −85°, preferably −78° C. for sufficient time to complete the reaction. After this preparatory treatment, the starting material is reacted with a compound of the formula:

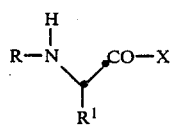

(III)

The chirality of the $R^1$ (4-position) substituent in Formula I is thus simply determined by the reactant of Formula III. Where D-alanine is employed, the compound of Formula I will be a pentanoic acid which is a 4-R compound.

In Step B, the product of the coupling reaction in Step A is reduced with zinc borohydride or hydrogen. This reduction converts the 3-oxo group to the desired 3-hydroxy group and also provides a chirality which is the same as that which has already been established at the 2-position. It is theorized that the zinc chelates the two carbonyls and the substituent at the 2-position and directs formation of the hydroxyl to correspond to the chirality of the 2-position substituent. Thus, 2S,3S compounds of Formula I are obtained.

In Step C, a nucleophilic reagent cleaves the oxazolidinone group from the remaining portion of the molecule, leaving the desired terminus. Thus, the acid, ester, or hydrazide is obtained.

The following example will further illustrate the method of the present invention, but is not intended to in any way be a limitation thereof.

EXAMPLE

STEP A: 3-(4-Methyl (2S,3S,4R)-4-t-butyloxycarbonylamino-3-hydroxy-2-methylpentanoate-t-butyloxycarbonylamino-3-oxo-2-methyl(pentanoyl)-4-(1-methylethyl)oxazolidin-2-one To a solution of 15 ml dry tetrahydrofuran containing lithium diisopropylamide (prepared from 7.58 mmole of diisopropylamine and 7.58 mmole of n-butyllithium) was added 1.17 g (6.32 mmole) of the N-(propanoyl) oxazolidinone at −78° C. under an inert atmosphere. The metallation was allowed to proceed for 2 hours. The resulting enolate was then transferred via cannula to a rapidly sitrring solution of t-Boc-D-alanine anhydride (10 mmole) in 60 ml of dry methylene chloride at −78° C. The addition was accomplished at a rate of approximately 3 ml/minute. After the transfer was complete, the reaction mixture was allowed to stand at −78° C. for 45 minutes more and was then quenched with a saturated ammonium chloride solution. The reaction mixture was diluted with 200 ml of diethyl ether and the organic phase was washed in succession with 20% sodium bicarbonate solution, 10% citric acid solution and brine. Rotoevaporation of the dried (MgSO$_4$) organic extracts afforded 2.1 g of the crude product as an oil. The analytical sample was obtained via flash chromatography on silica gel using hexane-ethyl acetate (4:1 v/v) as eluent. In this way, 1.13 g of a white solid was obtained which was recrystallized from ether/hexane to give white, feathery needles having an m.p. of 96.5–97.5.

Calc. for $C_{17}H_{28}N_2O_6$: N, 7.86; C, 57.26; H, 7.92. Found: N, 7.87; C, 57.09; H, 8.07.

PMR (MeOH-d$_4$): 0.90 and 0.93 (6H,2d,J=7), 1.27 and 1.30 (6H,2d,J=8), 1.45 (9H,S) 2.38 (1H,m), 4.32 (2H,m), 4.36 (1H,q,J=7), 4.43 (1H,m), 4.89 (1H,q,J=7).

STEP B: 3-(4-t-Butyloxycarbonylamino-3-hydroxy-2-methyl(-pentanoyl)-4-(1-methylethyl)-oxazolidin-2-one To a solution of 1.63 mmole of the ketone prepared in Step A above in 20 ml of dry diethyl ether was added, at −25° C., 10 mmole of a 0.2M solution of zinc borohydride in diethyl ether. After 1 hour, the reaction mixture was quenched at −25° C. with saturated ammonium chloride solution. The resulting mixture was warmed to room temperature and the phases were separated. The organic phase was washed with water and brine, then dried (MgSO$_4$) and evaporated to give the product as an oil. The analytical sample was available as a foam via preparative thick layer chromatography on silica gel (2:1 hexane-ethyl acetate elution in 95% isolated yield.

Calc. for $C_{17}C_{30}N_2O_6 \cdot \frac{1}{4}H_2O$: N, 7.73; C, 56.31; H, 8.48. Found: N, 7.50; C, 56.25; H, 8.64.

PMR (MeOH-d$_4$): 0.89 and 0.93 (6H,2d,J=7), 1.14 and 1.17 (6H,2d,J=7), 1.43 (9H,s), 2.31 (1H,m), 3.62 (1H,m), 3.75 (1H,dd,J=5,7), 3.96 (1H,p,J=7), 4.31 (2H,m), 4.49 (1H,m), 6.1 (1H,d,J=8).

STEP C: Methyl (2S,3S,4R)-4-t-butyloxycarbonylamino-3-hydroxy-2-methylpentanoate The oxazolidinone (0.33 mmole) prepared in Step B above was dissolved in 2 ml of dry methanol at 0° C.

and treated with a 1N sodium methoxide solution (0.69 mmole). The reaction was quenched after 1.5 hours by the addition of 10% citric acid solution. The reaction mixture was partitioned between ethyl acetate and brine. The phases were separated and the aqueous phase was extracted with ethyl acetate twice more. The combined organic extracts were dried (MgSO4) and concentrated to give an oil which was purified by silica gel chromatography (hexane-ethyl acetate 1:1 v/v). The desired methyl ester was obtained in 63% isolated yield as a clear oil which crystallized on standing.

PMR (CDCl3): 1.18 and 1.27 (6H,2d,J=7), 1.44 (9H,s), 2.67 (1H, dq,J=5,7), 3.0 (1H,brs), 3.71 (3H,s), 3.74 (2H,m), 4.,6 (1H,brd,J=9).

What is claimed is:

1. A method of preparing a compound of the formula:

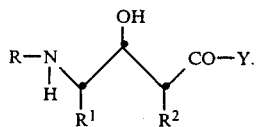

wherein:

R is hydrogen;

$R^1$ and $R^2$ are methyl and

Y is OH; and the configuration of the compound is (2S, 3S, 4R) comprising the following steps;

(a) treating an N-acyloxazolidinone of the formula:

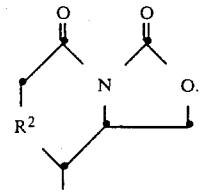

with lithium diisoprorylamide or lithium hexamethyl disilazide, followed by reaction with a compound of the formula:

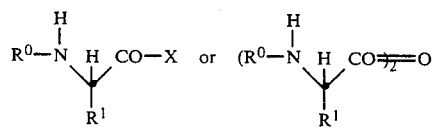

where X is a leaving group selected from Cl, Br, or pentafluorophenoxy, dinitrophenoxy and $R^0$ is t-butyloxycarbonyl or benzyloxycarbonyl; and the compound has a D-configuration;

(b) reducing the product of Step (a) with zinc borohydride to form the compound of the formula:

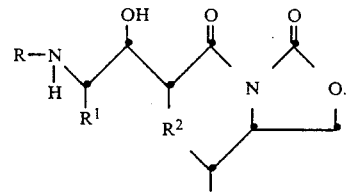

having a (2S, 3S, 4R) configuration; and (c) treating the product of Step (b) with potassium hydroxide to give a compound of Formula I having a (2S, 3S, 4R) configuration.

* * * * *